(12) United States Patent
Metelski (10) Patent No.: US 6,305,659 B1
(45) Date of Patent: Oct. 23, 2001

(54) STAND, IN PARTICULAR A MICROSCOPE STAND

(75) Inventor: Andreas Metelski, Romanshorn (CH)

(73) Assignee: Leica Microsystems AG (CH)

( * ) Notice: Subject to any disclaimer, the term of this patent is extended or adjusted under 35 U.S.C. 154(b) by 0 days.

(21) Appl. No.: 09/500,359

(22) Filed: Feb. 7, 2000

(30) Foreign Application Priority Data

Feb. 7, 1999 (CH) .................................................. 0266/99

(51) Int. Cl.⁷ .................................................. F12M 13/00
(52) U.S. Cl. .......................................... 248/519; 248/910
(58) Field of Search .................................. 248/519, 538, 248/910, 188.7; 359/393

(56) References Cited

U.S. PATENT DOCUMENTS

| | | | |
|---|---|---|---|
| 4,299,440 | * | 11/1981 | Hodgson .............................. 359/393 |
| 5,127,614 | * | 7/1992 | Etzold et al. ......................... 248/127 |
| 5,651,718 | * | 7/1997 | Nakamura .......................... 359/348 X |
| 5,684,628 | * | 11/1997 | Gerhard ................................ 359/391 |

OTHER PUBLICATIONS

Zeiss Germany: Carl Zeiss S5 Microscope Stand Product Literature—At least as early as Feb. 6, 1999.

* cited by examiner

Primary Examiner—Ramon O Ramirez
(74) Attorney, Agent, or Firm—Simpson, Simpson & Snyder, PLLC (57) ABSTRACT

The invention concerns a stand, in particular a microscope stand, having a multiple-part stand foot. The stand foot includes a removable stand foot body having cavities configured for enclosing and precisely positioning weights such that the weights can be installed without turning the stand foot over. A method for assembling such a stand is also described.

36 Claims, 6 Drawing Sheets

STAND, IN PARTICULAR A MICROSCOPE STAND

CROSS REFERENCE TO RELATED APPLICATION

Applicant claims foreign priority under 35 U.S.C. § 119 of Swiss Patent Application No. 0266/99 filed Feb. 7, 1999.

BACKGROUND OF THE INVENTION

A. Field of the Invention

The invention concerns a microscope stand used, for example, in connection with surgical microscopes, and a method for assembling a stand foot.

B. Description of the Prior Art

One of these stands with the designation "S5"0 offered by Zeiss has a hollow stand foot body into which weights can be inserted from the underside and can be secured or immobilized in the cavity of the stand foot body by way of transverse metal strips and bolts. The weights serve to improve the tipover resistance of the stand.

The disadvantage of this known construction is the great weight that results after installation of the weights. Because the weights must be installed from the underside, the stand foot must be placed on its upper side during assembly. After installation of the weights the stand foot, now heavier, must be turned over again. This is possible only with great exertion or with the assistance of several persons. The effect that is thus achieved by the division into multiple weights is partially canceled out again by this type of installation. Permissible working standards for one person are also thereby exceeded.

SUMMARY OF THE INVENTION

It is therefore an object of the invention to create an improved system and assembly method in which the total weight of the stand foot is never lifted up in the course of assembly, and in which the stand foot never needs to be turned over in the assembled state.

This object is achieved by a stand generally comprising a column and a stand foot for placement on a floor in a room, wherein the stand has at least one stand foot body that is or can be fitted with at least one weight. The stand also has a securing apparatus for securing the weight, wherein the securing apparatus can be actuated from the side of the stand foot that faces toward the room in the utilization position.

The fact that the securing apparatus is now usable from a side other than the underside of the stand foot eliminates the turning-over operation described above. This is advantageous not only during initial assembly, but also for each further assembly action, e.g. for transport purposes, service purposes, and demonstrations or the like.

The stand foot body includes a hollow body having at least one cavity, and the securing apparatus includes an assembly retainer and an immobilization apparatus that makes the cavity of the stand foot body closable on its side facing the floor in the utilization position. The immobilization apparatus is actuable from the side of the stand foot body that faces toward the room in the operating state. The weight can be roughly positioned on the assembly retainer, and at least two walls enclosing the associated cavity are configured such that they precisely position the weight during the immobilization operation. The immobilization apparatus preferably comprises at least one nut bolt coupling that passes through the stand foot body and makes the latter threadably joinable to the assembly retainer.

The stand foot body is configured with rotational symmetry about the vertical axis of the column, and has at its center a corresponding recess for the column. The recess includes a wedge that uses the column's own weight to press the column against the recess wall, and a bolt is preferably provided to extend radially through the wall of the recess to engage and clamp the column in place against the recess wall.

The invention also encompasses a method for assembling a stand. The method includes providing an assembly retainer, roughly positioning at least one weight on the assembly retainer, providing a threaded rod extending approximately from the center of the assembly retainer, slipping a hollow stand foot body over the assembly retainer and onto the weight or weights so that the threaded rod passes through a hole in the stand foot body and each weight resides within a cavity defined by the stand foot body, and tightening a nut on the threaded rod such that two or more cavity walls simultaneously precisely position each weight.

BRIEF DESCRIPTION OF THE DRAWINGS

Details of the present invention are evident from the drawings, which depict an exemplary embodiment according to the present invention. The figures are described in overlapping fashion; identical reference characters denote identical components. Functionally identical components having possibly different conformations bear identical reference numbers with different letter indices. The figures do not limit the invention, but merely indicate exemplary embodiments of the invention. The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 1:
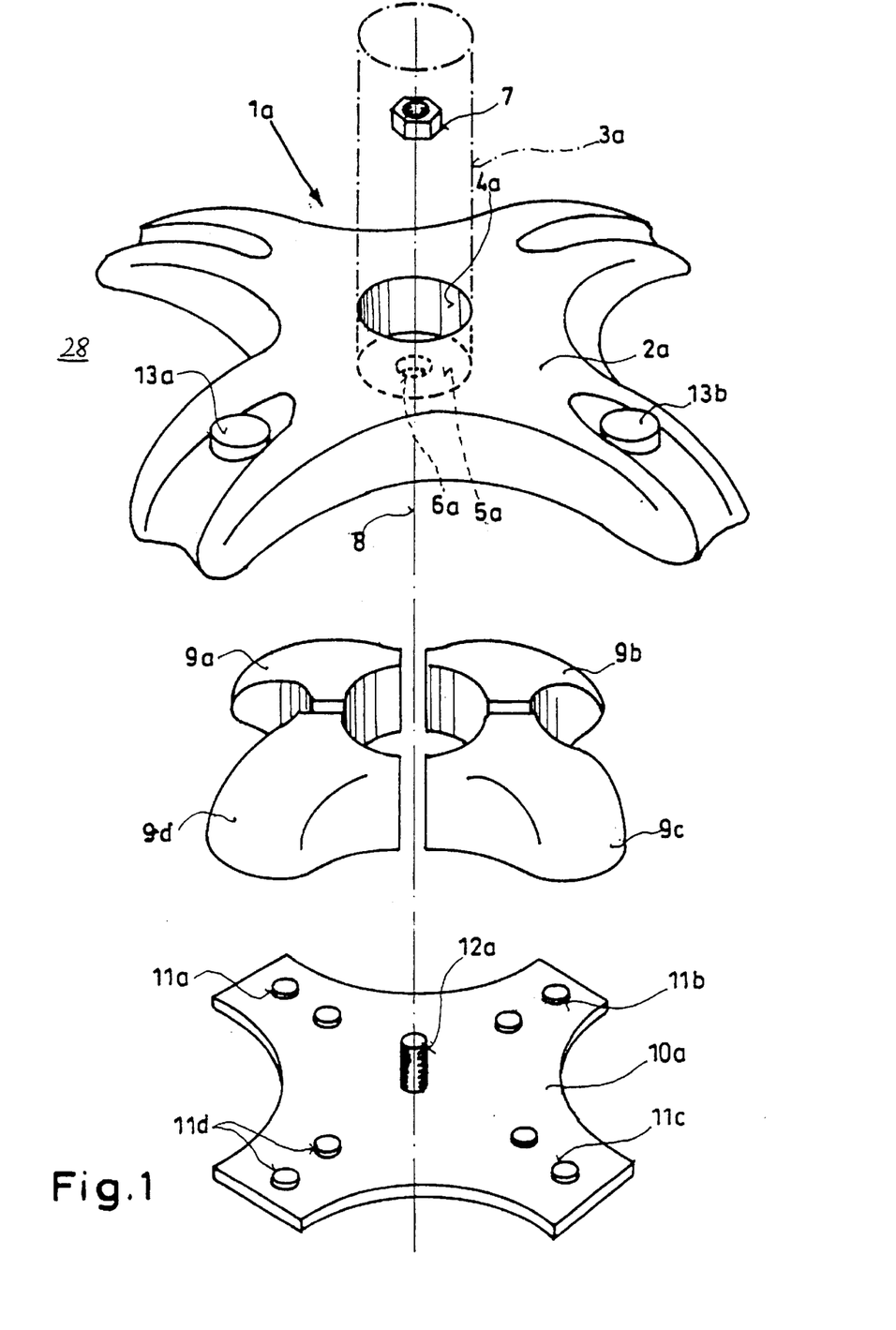
FIG. 1 shows an exploded view of a stand according to the present invention in a schematic depiction, prior to assembly.

One of the preferred embodiments of the invention is evident from FIG. 1. On an assembly retainer 10a that lies on the floor in the utilization position, four individual weights 9a–d are roughly by way of lugs 11a–d and counterpart lug recesses (see recesses 21a–h in FIG. 5) in weights 9a–d. Precise positioning and immobilization of weights 9a–d is accomplished by setting in place a stand foot body 2a that has corresponding cavities for receiving weights 9a–d. Stand foot body 2a has, in the center, a recess 4a terminating at a base 5a, which can be a plate or configured in one piece with the stand foot body. A hole 6a passes through base 5a and fits onto a threaded rod 12a that is immovably joined —e.g. thread-joined, pressed, or welded—to assembly retainer 10a. For immobilization, a nut 7 is threaded onto this threaded rod 12a until assembly retainer 10a is braced by way of weights 9a–d against stand foot body 2a. Precise positioning of weights 9a–d is thus accomplished by the walls that delimit the cavity or cavities of stand foot body 2a. In particular, it is conically configured walls that bring about this precise positioning.

The weights 9a–d are preferably be made of primed and/or painted gray cast iron, steel, brass, or other heavy metal. The stand foot body 2a is preferably manufactured from aluminum, in particular die-cast aluminum.

Stand foot 1a serves also to receive a column 3a that can be anchored in recess 4a. Stand foot 1a carries not only transport casters 14 (not shown in FIG. 1), but also two brakes, of which brake pedals 13a,b are indicated in FIG. 1.

Figure 2:
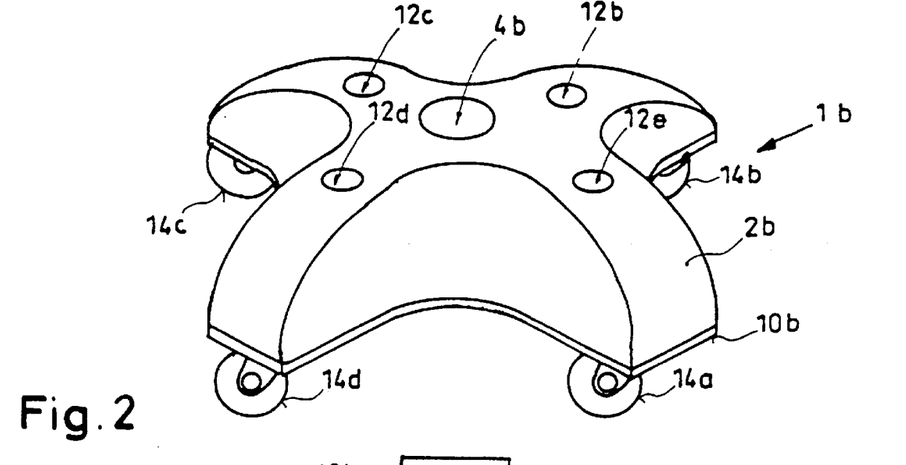
FIG. 2 shows a variant of the configuration of FIG. 1.

The variant 1b according to FIG. 2 also has a stand foot body 2b that is constructed from four arm-like stand foot body parts. Each part has a cavity for reception of a weight. Each part is thread-joined from the top together with the weight enclosed in the cavity, by way of threaded rods 12b–e, to an assembly retainer 10b in a manner identical or similar to the configuration according to FIG. 1.

As a variant thereof, the bolts could also pass through weights 9e–h laterally, and in the assembled position could lie approximately horizontal with respect to floor 28. This still allows access from the room, but on the other hand reduces the area subject to dirt penetration on the upper side of the weights.

Here as well, the effect desired in accordance with the present invention is thus achieved, and assembly can occur from above. The configuration of stand foot body 2b could, of course, also be one-piece. The purpose of the depiction of FIG. 2 is to indicate that according to the present invention, multiple bolts can also be used to join the stand foot body to the assembly retainer.

It should also be mentioned that variants in which a bolt can be threaded from top to bottom into the assembly retainer through the stand foot body, and optionally through the respective weight, are also within the context of the invention. Other types of immobilization, for example clamps or the like slid on laterally, are also encompassed, but the variants depicted are preferred.

Figure 5:
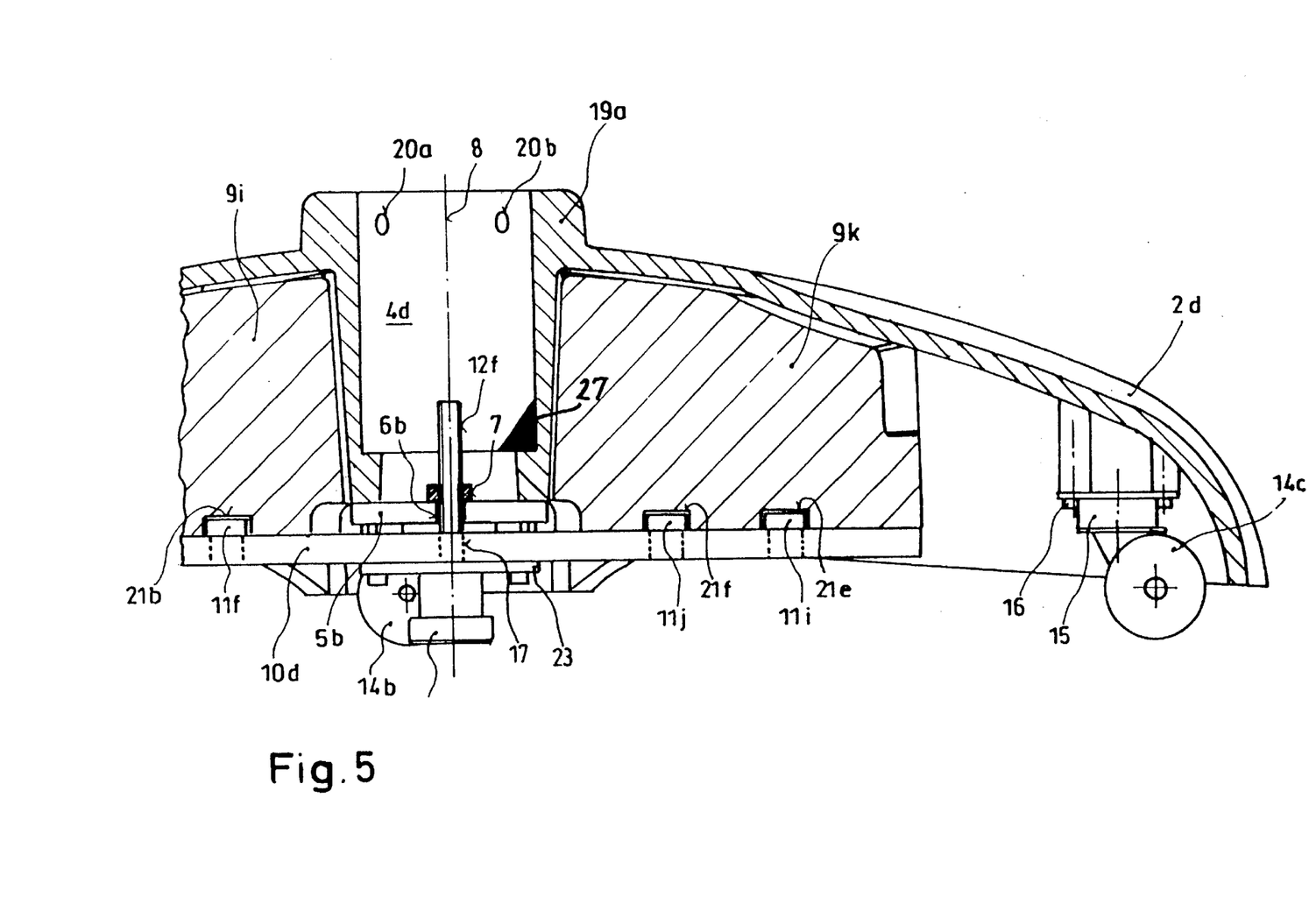
FIG. 5 shows an embodied variant of the configuration of FIG. 1 in a lateral section through the stand foot body.

FIG. 2 also serves to indicate the possibility provided according to the present invention of joining transport casters 14a–d to assembly retainer 10b so that in contrast to FIG. 5, for example, casters 14a–d are not joined directly to stand foot body 2b.

Figure 3:
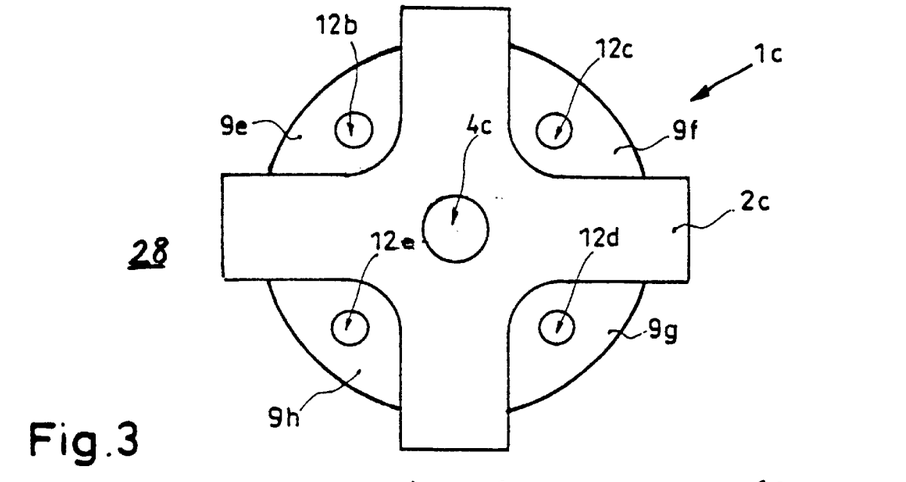
FIG. 3 shows a further variant of the configuration of FIG. 1 in plan view.
Figure 4:
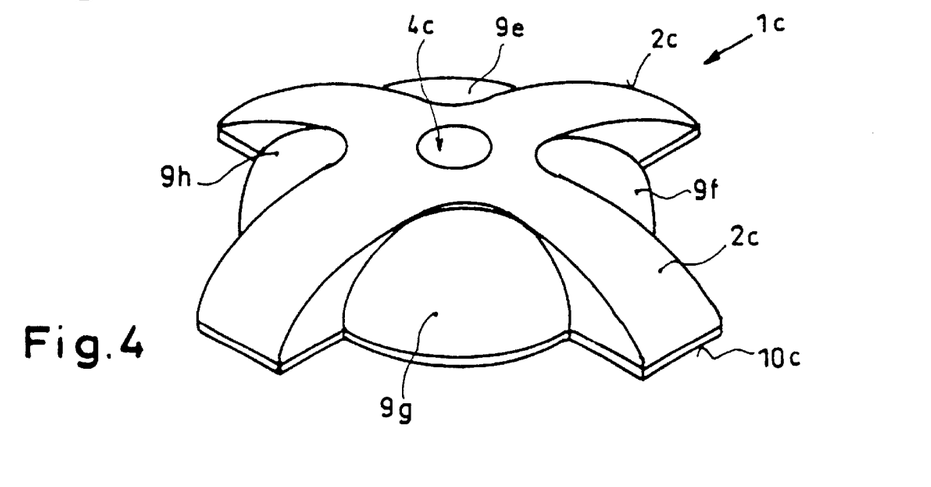
FIG. 4 shows the configuration of FIG. 3 in an oblique view.

FIG. 3 shows a further variant 1c in which the weights are not received by way of a cavity but rather are bolted laterally onto stand foot body 2c. This variant is not preferred for reasons associated with sterilization of the surgical microscope stand, since gaps remain between weights 9e–h. For less critical areas, however, this simple configuration is advantageously usable. With this configuration it is also conceivable to do without an assembly retainer, by bolting weights 9e–h directly onto stand foot body 2c. With this configuration, threaded rods 12b–e (indicated only symbolically) or bolts can also be threaded obliquely into stand foot body 2c or can project obliquely out of it. FIG. 4 shows the configuration of FIG. 3 in an oblique view.

Figure 6:
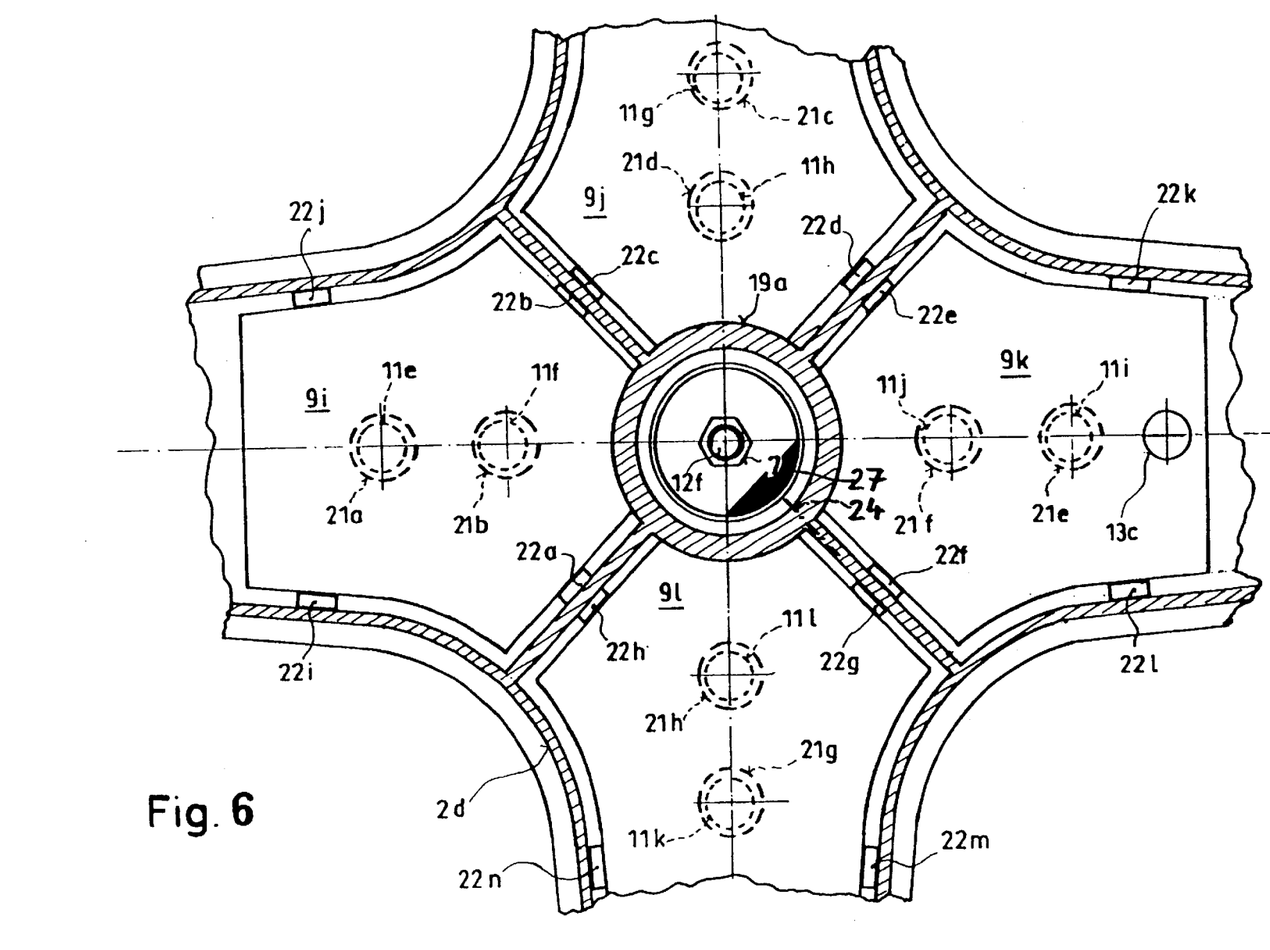
FIG. 6 shows a plan view of the configuration according to FIG. 5.

The configuration of the stand foot 1d as shown in FIGS. 5 and 6 is a preferred embodiment. In addition to what has already been described, a particular shaping of the weights 9i–l with lug recesses 21a–h is evident. The lug recesses can of course be shaped differently in order, if applicable, to provide a greater degree of freedom for precise positioning. Located opposite lug recesses 21a–b are lugs 11e–l, which are rivet-like in appearance and preferably are made from plastic. They are anchored in holes of assembly retainer 10d. The advantage of such plastic lugs lies in the lower risk of abrasion on the weights that, for example, are not made from corrosion-proof material. Although according to a particular embodiment such weights are preferably primed or painted, abrasion which might expose the corroding material is nevertheless possible, specifically at lug engagement points. This is effectively prevented by the plastic. A side from this, the lugs and lug recesses can also be configured so that in the assembled state, the underside of weights 9i–l is spaced away from the upper side of assembly retainer 10d, so that weights 9i–l rest on lugs 11e–l. As an alternative to this, foam strips could also be introduced between the underside of the weights and the upper side of the assembly retainer, so that the weights are protected on all sides from mechanical abrasion and are also vibration-damped. Transport casters 14b,c are conventional casters mounted to stand foot body by bolts 16 extending through caster base 15.

Recess 4d has, in the region of its support wall 19a, at least one threaded hole 20a,b that, with a bolt (not shown), serves to immobilize column 3a (not shown in FIGS. 5 and 6).

As a special feature, the configuration shown in FIGS. 5 and 6 has a threaded-in threaded rod 12f that has on its end facing toward assembly retainer 10d a hex nut 7 with which it can be threaded into assembly retainer 10d. Threaded or press fit mounting are indicated for portion 17 in FIG. 5. For safety, this region can be covered with cover plate 23.

FIG. 6 shows, by way of example, foam strips 22a–m that are applied onto the walls of stand foot body 2d delimiting the respective cavities, and in the assembled state ensure that weights 9i–l fit in wobble-free and damped fashion in the cavities. Thus, they also provide clearance compensation.

Also indicated is an oblique surface or wedge 27 that is preferably used, and a symbolically indicated bolt 24, which are described in more detail in connection with the variant of FIG. 7.

Figure 7:
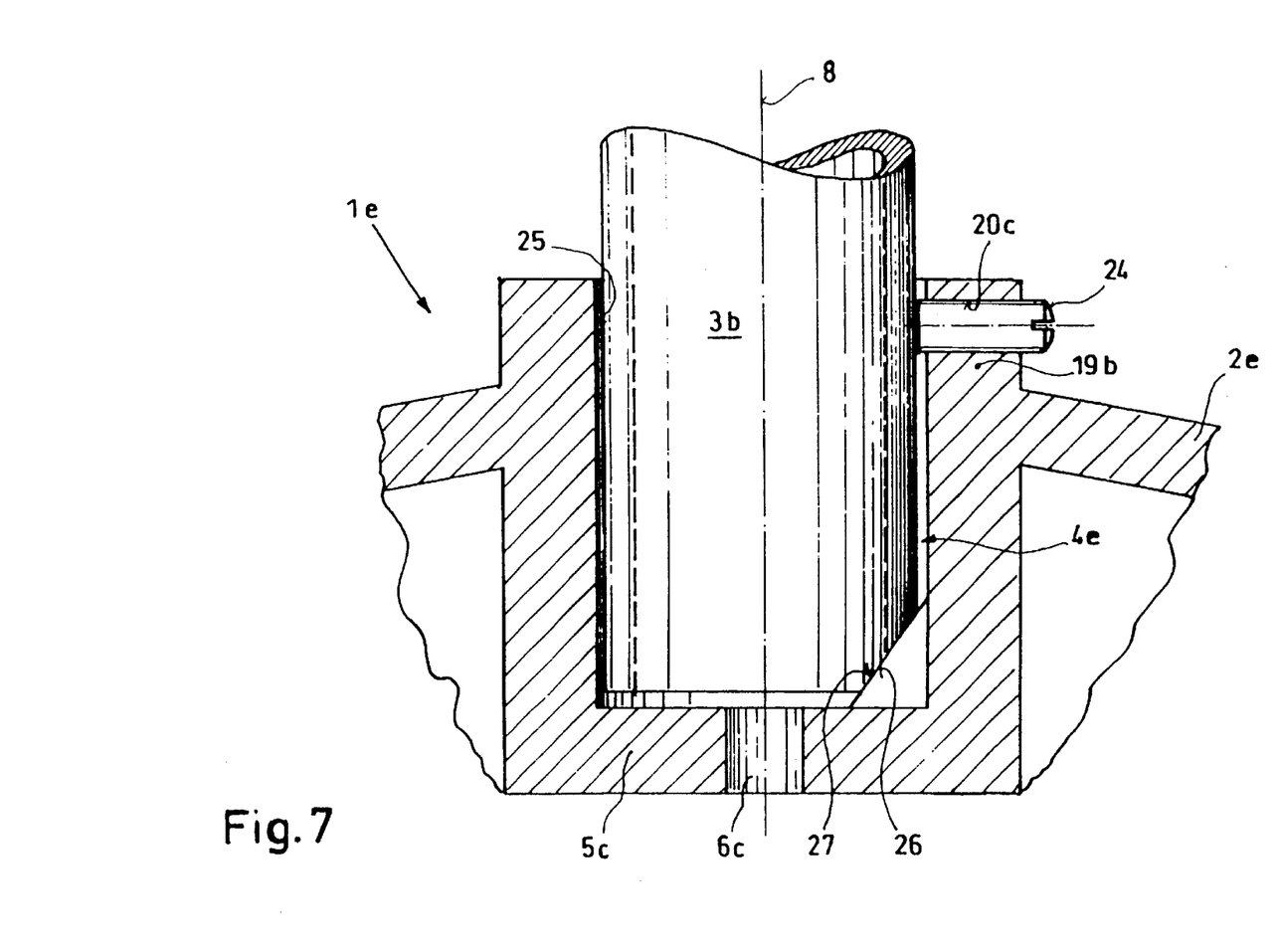
FIG. 7 shows a detail of a variant of the configuration of FIG. 5.

The particular detail in FIG. 7 shows a portion of a stand foot body 2e that has a wedge 26 in its recess 4e in the region of recess base 5c. This wedge 26, by way of its oblique surface 27, exerts a lateral sliding force on the inserted column 3b, so that the latter is positively pressed by the sliding force against wall 25 of recess 4e located opposite the wedge. As shown, column 3b preferably includes a corresponding oblique surface contacting surface 27. Since this wall is perpendicular to the floor in the operating position, the column is thus also oriented vertically, regardless of diameter tolerances. A quasi-centering effect is thereby achieved. The center of the column can be displaced slightly out of the center of the stand foot (within the tolerance range of recess 4e and column 3b). The stand can also have a bevel in the region of 27, but this is not mandatory. The advantage of this configuration, which can also be used independently of the other stand foot configurations according to the present invention, is that the stand can be attached easily with only one clamping bolt 24, but nevertheless is securely "centered".

According to a particular embodiment of the invention, recess 4 in stand foot body 2 is protected from wear. This can be brought about, for example, by way of a steel bushing in the recess of an aluminum stand foot body.

Figure 8:
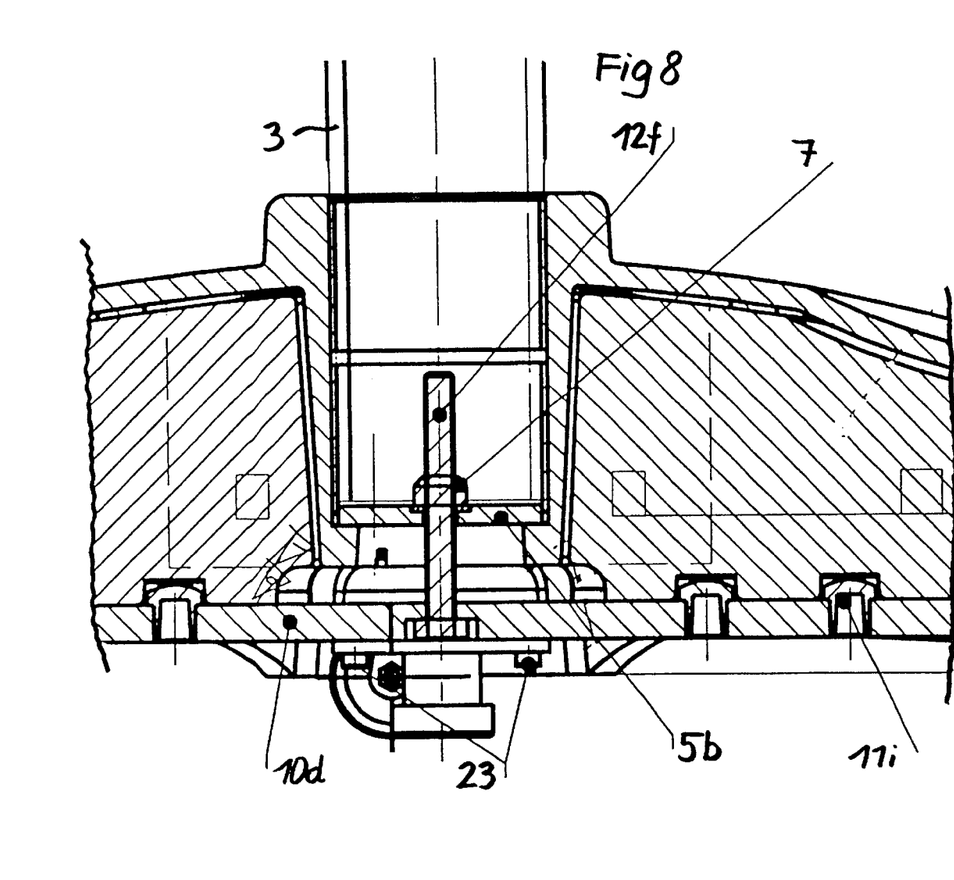
FIG. 8 shows a detail variant of FIG. 5.
Figure 9:
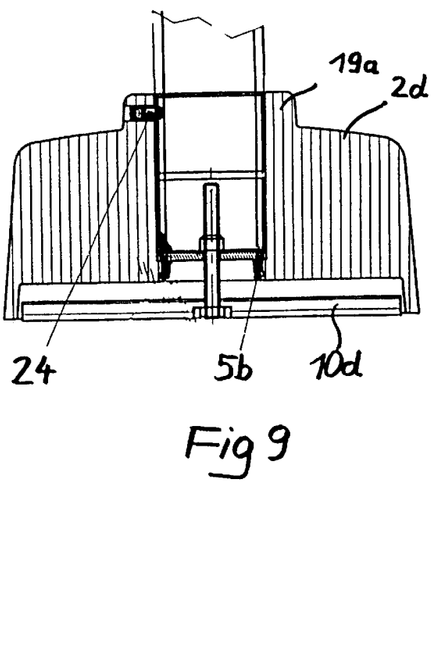
FIG. 9 shows a section through the wall of a stand foot body according to FIG. 8 between adjacent star-shaped arms.

For assembly purposes, plate 5b shown in FIG. 5 can also be attached to stand foot body 2d by way of bolts (not shown). A variant of this is depicted in FIG. 8. Plate 5b is in this case placed not from below but from above onto a radial projection of the wall of the stand foot body. Bolt 12f is held at its lower end with a nut on assembly retainer 10d. In this example, lugs 11i are mushroom-shaped and made of plastic.

In all the figures, the assembly retainer is depicted as a baseplate. The invention also, however, encompasses variants in which a baseplate is absent and the weights can be attached to an assembly retainer that is shackle-shaped in section, and thus in the assembled state do not rest on the assembly retainer but rather hang from it. In alternatives thereto, neither the baseplate nor a shackle-shaped assembly retainer is present. With these alternatives, support extensions are provided on the stand foot body or the like for the weight or weights, the weight or weights being thread-joined to the stand foot body. Such support extensions may be imagined, for example, in FIG. 4 instead of baseplate 10c. They would be joined, for example, to stand foot body 2c at its lower edge, and thus would support weights 9e–h just as in the exemplary embodiment illustrated.

It is preferred that the assembly retainer 10, stand foot body 2, and each weight 9 have a maximum weight defined in the context of permissible working standards for handling by one person. Typically, this is in the range of about 10–25 kg each.

List of Reference Characters:

| 1 | Stand foot | a, b, c, d, e |
|---|---|---|
| 2 | Stand foot body | a, b, c, d, e |
| 3 | Column | a, b |
| 4 | Recess | a, b, c, d, e |
| 5 | Base of recess | a, b, c |
| 6 | Hole | a, b, c |
| 7 | Nut | |
| 8 | Column axis | |
| 9 | Weight(s) | a–d, e–h, i–l |
| 10 | Assembly retainer | a, b, c, d |
| 11 | Lugs | a–d, e–l |
| 12 | Threaded rod | a, b–e, f |
| 13 | Brake pedal | a–b, c |
| 14 | Transport casters | a–d |
| 15 | Caster base | |
| 16 | Bolt | |
| 17 | Press fit or threaded fit | |
| 19 | Support wall | a, b |
| 20 | Threaded hole | a, b, c |
| 21 | Lug recess | a–h |
| 22 | Foam strip | a–m |
| 23 | Cover plate | |
| 24 | Clamping screw | |
| 25 | Wall | |
| 26 | Wedge | |
| 27 | Oblique surface | |
| 28 | Floor | |

What is claimed is:

1. A stand comprising
 a stand foot for placement on a floor of a room, said stand foot including a stand foot body fitted with at least one removable weight and a securing -apparatus for releasably securing said weight, wherein said securing apparatus can be actuated from a side of said stand foot that faces toward said room in the utilization position; and
 a column supported in an upright position by said stand foot.

2. The stand according to claim 1, wherein the stand foot body comprises a hollow body having at least one cavity, and said securing apparatus comprises an assembly retainer and an immobilization apparatus for making said at least one cavity closable on its side that faces toward said floor in the utilization position, said immobilization apparatus being actuable from a side of the stand foot body that faces toward said room in said utilization position.

3. The stand according to claim 2, wherein said at least one weight is roughly positioned on said assembly retainer, and said at least one cavity includes at least two walls configured such that said at least two walls precisely position said at least one weight during actuation of said immobilization apparatus.

4. The stand according to claim 3, wherein at least one of said at least two walls is configured on its side facing toward said at least one weight in a manner widening substantially conically away from said floor.

5. The stand according to claim 3, wherein at least one of said at least two walls is coated with an elastic layer.

6. The stand according to claim 5, wherein said elastic layer is made of a foamed material.

7. The stand according to claim 3, wherein said assembly retainer is coated with an elastic layer.

8. The stand according to claim 7, wherein said elastic layer is made of a foamed material.

9. The stand according to claim 3, wherein said at least one weight includes a plurality of lug recesses arranged to coat with counterpart lugs provided on said assembly retainer for said rough positioning.

10. The stand according to claim 9, wherein said lugs are made of plastic.

11. The stand according to claim 9, wherein one of said plurality of lug recesses is cylindrical and others of said plurality of lug recesses are configured as oblong holes.

12. The stand according to claim 2, wherein said immobilization apparatus is actuable from a side of said stand foot body facing toward said column.

13. The stand according to claim 12, wherein said immobilization apparatus comprises at least one nut/bolt coupling that passes through said stand foot body and makes said stand foot body threadably joined to said assembly retainer.

14. The stand according to claim 13, wherein a plurality of said weights is provided, and said nut/bolt coupling is arranged in the center of said stand foot body and thus also centrally with respect to said plurality of weights.

15. The stand according to claim 13, wherein said nut/bolt coupling is of a self-locking configuration.

16. The stand according to claim 13, wherein said nut/bolt coupling is equipped with a rotation lock.

17. The stand according to claim 2, wherein said stand foot body is configured in the shape of a star having a plurality of arms, wherein each of said plurality of arms includes one said cavity for receiving an associated weight.

18. The stand according to claim 17, wherein said weight is roughly positioned on said assembly retainer, and at least two walls of each said cavity are configured such that they precisely position said associated weight during actuation of said immobilization apparatus.

19. The stand according to claim 18, wherein at least one of said at least two walls is configured on its side facing toward said associated weight in a manner widening substantially conically away from said floor.

20. The stand according to claim 2, wherein said assembly retainer, said stand foot body, and said at least one weight each have a maximum weight defined in the context of permissible working standards for handling by one person in the range of 10–25 kg each.

21. The stand according to claim 1, wherein said stand foot body is configured in the shape of a star having a plurality of arms, wherein each of said plurality of arms receives an associated weight.

22. The stand according to claim 21, wherein each of said plurality of arms includes a cavity for enclosing said associated weight.

23. The stand according to claim 21, wherein each of said plurality of arms includes a support extension for supporting associated weight.

24. The stand according to claim 21, wherein each of said plurality of arms includes a caster.

25. The stand according to claim 1, wherein said at least one weight is made of cast iron.

26. The stand according to claim 1, wherein said at least one weight is made of steel.

27. The stand according to claim 1, wherein said at least one weight is made of brass.

28. The stand according to claim 1, wherein said at least one weight is primed or painted.

29. The stand according to claim 1, wherein said stand foot body is manufactured from aluminum.

30. The stand according to claim 29, wherein said stand foot body is manufactured from die-cast aluminum.

31. The stand according to claim 1, wherein said at least one weight is vibration damped with respect to said stand foot body.

32. The stand according to claim 1, wherein said at least one weight is vibration damped with respect to said assembly retainer.

33. The stand according to claim 1, wherein said stand foot body is rotationally symmetrical about a vertical axis of said column, said stand foot body including a centrally located recess terminating at a base and a wedge-shaped projection extending from said base and deviating from said rotational symmetry, whereby said column is pressed against a lateral wall of said recess under influence of its own weight.

34. The stand according to claim 33, further comprising a bolt extending radially through a wall of said recess to positively clamp said column against said lateral wall.

35. The stand according to claim 33, wherein said column includes an inclined surface corresponding to an opposing inclined surface of said wedge-shaped projection.

36. A method for assembling a stand comprising the steps of:

(A) providing an assembly retainer having a threaded stem fixed at an approximately central location thereof;

(B) roughly positioning at least one weight on said assembly retainer;

(C) slipping a hollow stand foot body over said assembly retainer and onto said at least one weight, said stand foot body having a central hole through which said threaded stem passes and a cavity having at least two walls surrounding said at least one weight; and (D) threading a nut onto said threaded stem until said assembly retainer is immovably joined to said stand foot body and said at least one weight is precisely positioned on said assembly retainer by said at least two walls.

* * * * *